United States Patent [19]

Martell

[11] Patent Number: 4,732,162
[45] Date of Patent: Mar. 22, 1988

[54] AUTOMATIC AND POSITION-SENSITIVE SYRINGE AND METHOD FOR NONASPIRATING OR ASPIRATING OBTAINING OF BLOOD SAMPLES

[75] Inventor: Michael D. Martell, Riverside, Calif.

[73] Assignee: Martell Medical Products, Inc., Riverside, Calif.

[21] Appl. No.: 73,361

[22] Filed: Jul. 6, 1987

Related U.S. Application Data

[63] Continuation of Ser. No. 789,233, Oct. 18, 1985, abandoned.

[51] Int. Cl.$^4$ .......................... A61B 5/14; A61M 5/00
[52] U.S. Cl. ...................... 128/765; 128/766; 604/190
[58] Field of Search ............... 128/763, 765, 766, 760; 604/190, 222, 405, 406

[56] References Cited

U.S. PATENT DOCUMENTS

| | | | |
|---|---|---|---|
| 3,557,778 | 1/1971 | Hughes | 128/766 |
| 4,099,520 | 7/1978 | Decker et al. | 128/766 |
| 4,207,870 | 6/1980 | Eldridge | 128/764 |
| 4,305,406 | 12/1981 | Megahed | 128/766 |
| 4,317,456 | 3/1982 | Percarpio | 128/766 |
| 4,424,817 | 1/1984 | Williams | 128/766 |
| 4,448,206 | 5/1984 | Martell | 128/765 |
| 4,466,446 | 8/1984 | Baidwam et al. | 128/765 |

Primary Examiner—Edward M. Coven
Assistant Examiner—John C. Hanley
Attorney, Agent, or Firm—Gausewitz, Carr & Rothenberg

[57] ABSTRACT

A syringe for sampling blood has a handle driven plunger in which is mounted an air permeable filter in communication with a valve chamber. In the chamber is mounted a gravity driven steel ball that is heavy enough to enable the syringe to be used in aspiration, with the ball remaining seated to block the air flow through the valve, and yet light enough to be used in taking of a normal pressure arterial blood sample during which air flow through the filter will drive the ball from its seat.

15 Claims, 5 Drawing Figures

AUTOMATIC AND POSITION-SENSITIVE SYRINGE AND METHOD FOR NONASPIRATING OR ASPIRATING OBTAINING OF BLOOD SAMPLES

BACKGROUND OF THE INVENTION

This is a continuation of application Ser. No. 789,233 filed Oct. 18, 1985, abandoned, for Automatic and Position-Sensitive Syringe and Method for Nonaspirating or Aspirating Obtaining of Blood Samples.

In my prior U.S. Pat. No. 4,448,206 there is disclosed an aspirating syringe having various advantages over the prior art. Such advantages are indicated, for example, in columns 2 and 3 of the patent, as well as columns 5 and 6 thereof.

Applicant has now invented an improvement over U.S. Pat. No. 4,448,206, as well as over various other prior-art patents. Such improvement has the advantages described in U.S. Pat. No. 4,448,206 and also has additional important advantages.

These advantages include a gravity-responsive and position-responsive ball check valve mounted in the plunger. The ball of the valve is sufficiently heavy to effectively seal with the plunger for aspiration of blood, but sufficiently light that air may vent from the tubular body during taking of an arterial sample under arterial pressure without sealing. Furthermore, the relationships are such that when the syringe is held at an incorrect angle, as by relatively inexperienced personnel, aspiration may not be effected to any substantial extent. The valve is employed in combination with an air-permeable but blood-impermeable filter, such filter preventing blood from reaching the ball. Air can be vented at all times from the tubular body of the syringe, through the filter and past the ball, regardless of the position of the syringe. The only time air does not vent is when aspiration is occurring, while the syringe is in a desired orientation relative to the horizontal, the ball then being seated by gravity and preventing flow of air past the valve seat and through the filter to thereby effect a highly satisfactory aspiration operation as the plunger is moved upwardly.

SUMMARY OF THE INVENTION

There is seated over an air-venting passage in the plunger of a syringe for single in vitro diagnostic use, a ball that is sufficiently heavy that it will respond to gravity despite frictional, electrostatic or other forces, but sufficiently light that air may vent during taking of an arterial sample without aspiration or aspirating. Because of the ball, there is no need for any lost-motion connection to effect manual closing of the valve when aspiration is desired.

The region around the seat for the ball is inclined at a predetermined angle related to the desired angle at which the syringe should be held during drawing of a blood sample. The relationship is such that aspiration may not occur to any substantial degree when the syringe is at an excessively small angle relative to the horizontal. This prevents an inexperienced operator from holding the syringe at an improper angle during aspiration.

The plunger has incorporated therein a filter which is permeable to air but not permeable to blood. Preferably, the ball is mounted on the side of the filter remote from the needle, so that no blood ever contacts the ball. The ball and filter collaborate with each other to effect venting of air when desired.

The apparatus further comprises a nipple that maintains the ball relatively close to its seat at all times, so that the ball does not rattle around in the syringe to any substantial extent, and so that the ball seats rapidly whereby aspiration may occur.

Means are provided to effect a continuous, uninterrupted flow path for air between the forward end of the syringe and the outer end thereof, the only time such flow path is blocked being when the ball is seated, as during aspiration.

In accordance with the method, a ball is mounted on the air-venting path through the plunger of a syringe for single in vitro diagnostic use, following which the syringe is held at such an angle that the ball will seat, following which the syringe is operated to withdraw the plunger and thus aspirate blood into the sample chamber. When blood is introduced into the syringe by arterial pressure instead of by aspiration, the ball is lifted by air pressure off of its seat so that air may vent from the blood-sample chamber. Thus, the method comprises a ball that is sufficiently heavy to seat effectively for aspiration purposes, but sufficiently light that it will not interfere with air venting during taking of a sample by arterial pressure.

The method further comprises so constructing the region around the ball that the ball will not seat unless the syringe is at a substantial angle to the horizontal, the result being that inexperienced personnel may not operate the syringe improperly during aspiration.

DETAILED DESCRIPTION OF THE PREFERRED EMBODIMENT

Figure 1:
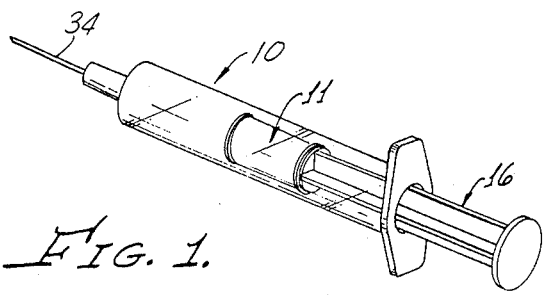
FIG. 1 is an isometric view of a syringe incorporating the present invention.

The disclosure of my prior U.S. Pat. No. 4,448,206 is hereby incorporated by reference herein. Thus, a description of the materials employed, and other factors and relationships relating to the basic construction of the syringe, will not be repeated in this specification. The present specification will, instead, be directed toward relationships and the material that differs from what is described in the U.S. Pat. No. 4,448,206.

Stated generally, the preferred embodiment of the syringe has a tubular body 10 in which a plunger 11 is slidably mounted. The main body of the plunger is formed of a soft elastomeric material, as described in the above-cited patent, and contains an air-permeable and blood-impermeable filter 12. The region between the forward end of the plunger 11 and the forward end of body 11 may be termed a sample chamber, and is numbered 14.

Plunger 11 is moved longitudinally of body 10 by a handle 16 which is an extension of the plunger. Stated more specifically, the inner end disc 17 of handle 16 has projecting axially therefrom a cylindrical extension 18. Fixedly mounted on extension 18, at the inner end thereof and concentric therewith, is a disc or nipple 19 the diameter of which is much smaller than that of disc 17. The handle 16 is connected to plunger 11 by inserting the disc 19 through an axial passage at the outer end of plunger 11, the wall 21 of the passage being cylindrical and coaxial with the axis of the syringe.

The disc or nipple 19 is disposed in a chamber 22 near the outer end of plunger 11. The chamber 22 is sufficiently large to freely receive the disc 19 and also a ball described subsequently. There is a large clearance between the periphery of disc 19 and the wall of chamber 22, such wall being cylindrical and numbered 23.

Figure 2:
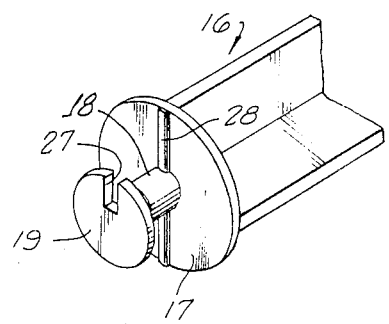
FIG. 2 is a fragmentary isometric view of only the inner end of the handle of the syringe, and illustrating the air-venting means of the handle.

There is a continuous vent passage from sample chamber 14 to the outer end of body 10, at all times except when aspiration is occurring. Aspiration occurs only when the syringe is at a proper angle relative to the horizontal, the passage then being blocked by a ball as described subsequently. Such passage is through the filter 12, then through an axial passage 24 in plunger body 11, such passage 24 having a cylindrical wall 26 coaxial to the plunger and the body 10, then through the chamber 22, then through passage 21, then through a space between the outer end of plunger body 11 and the disc 17, and then through the body 10 around the X-sectioned handle 16. To ensure that such passage is present, there is a large notch 27 (FIG. 2) in disc or nipple 19, the notch extending inwardly to a region spaced inwardly from wall 21 of the axial passage between chamber 22 and the region of the syringe outwardly of the plunger 11. Furthermore, radial ridges or beads 28 are molded on the inner face of handle disc 17, such ridges or beads serving as spacers that prevent the inner surface of disc 17 from engaging the outer end of plunger body 11 and thereby blocking the passage circumscribed by wall 21. The diameter of disc 17 is substantially smaller than the inner diameter of the tubular body 10 of the syringe. The diameter of extension 18 of the handle is also substantially smaller than is the diameter of passage wall 21 therearound.

Extension 18 has a length somewhat greater than that of the passageway 21, to aid in assembly of the apparatus. It is pointed out, however, that no lost-motion connection is required for functional purposes because there need be no valve action except by the ball valve to be described.

Disposed in chamber 22 between disc 19 and passage 24 is a ball 31. The ball is adapted to seat on a frustoconical surface 33 of which the innermost end forms an annular seat 32 at the outer end of the cylindrical passage 24. The ball is formed of nonbuoyant material, preferably steel. The ball has a diameter sufficiently large, and a weight sufficiently great, that it will seat effectively on seat 32. On the other hand, it has a weight sufficiently small that it will move off seat 32 and permit venting of air from sample chamber 14 through filter 12 when blood is being introduced into the sample chamber under arterial pressure. Such air, initially within the sample chamber, vents through the above-described air passage through filter 12, passage 24, chamber 22, notch 27 and the region around the periphery of disc 19, the annulus between extension 18 and cylindrical wall 21, the space between the interface of disc 17 and the rear face of the body of the plunger 11, the space between the periphery of disc 17 and the inner wall of tubular body 10, and the region around the X-shaped handle 16.

Figure 4:
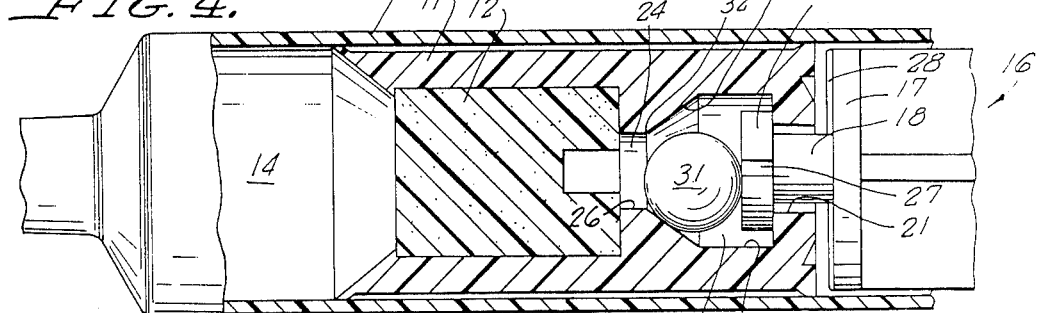
FIG. 4 corresponds to FIG. 3 but shows the syringe in a horizontal position after the handle has been pulled outwardly to increase the space between the nipple and the ball seat.
Figure 5:
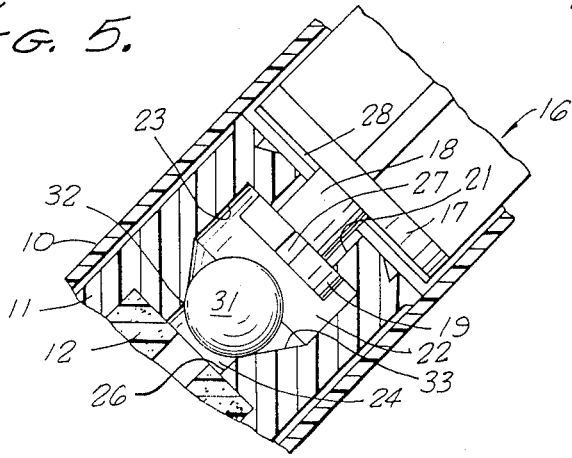
FIG. 5 shows the ball in effectively seated condition preparatory to aspirating operation, the syringe being at a proper angle to the horizontal.

When the handle is in retracted position (FIGS. 4 and 5), the disc or nipple 19 is maintained sufficiently close to valve seat 32 that the ball 31 will not rattle around, and will seat rapidly when desired. When the handle is retracted, the space between disc 19 and valve seat 32 is sufficient that ball 31 may move far enough off the seat for air-flow purposes (as shown in FIG. 4). Conical surface 33, which extends at an angle of about 45 degrees to the syringe axis, forms a guide for the ball to assist the ball in moving between open (FIG. 4) and closed (FIG. 5) positions. Conical surface 33 forms an outwardly-diverging guide surface within the valve chamber 22 that cooperates with the steel ball 31 to enable the ball to be gravity driven onto the valve seat, thereby blocking air flow through the passage 24, whenever the axis of the syringe is at an angle to the vertical that is not greater than a predetermined angle such as about 45 degrees, for example. The frustoconical guide surface 33 also cooperates with the ball and acts to prevent the ball from being gravity driven onto its valve seat when the axis of the syringe is at an angle to the vertical greater than the predetermined angle.

The ball will move off its seat when the syringe is used for taking a sample of normal-pressure arterial blood. It will also move off its seat when the syringe axis is at an angle to the vertical of more than about 45 degrees. In the position shown in FIG. 4, with the syringe horizontal, or nearly so, the ball will be gravity displaced from the seat to the extent permitted by the position of the handle disc 19.

Figure 3:
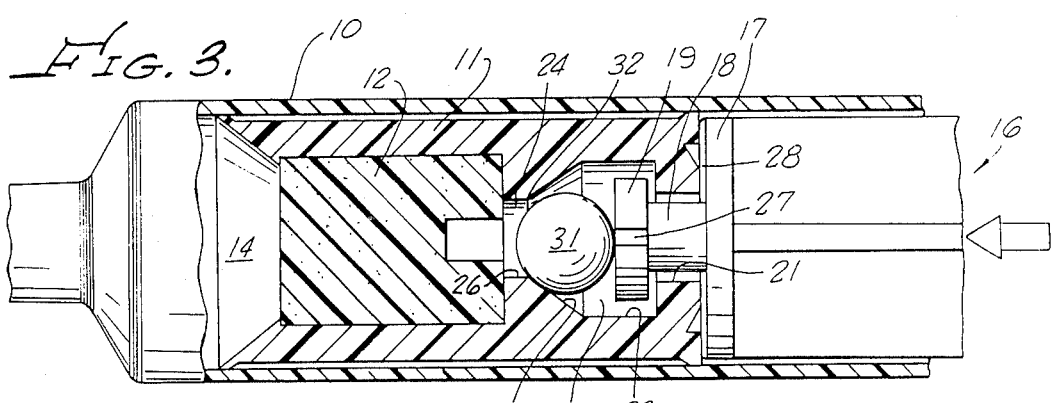
FIG. 3 is an enlarged longitudinal sectional view showing the syringe in a horizontal position and with the handle being pressed inwardly to its limiting position.

In a presently-preferred embodiment, the part sizes and configurations are such that even when the handle is pressed inwardly, toward the left as viewed in FIG. 3, to its limiting position (limited by abutment of ridges 28 and disc 17 upon end surface of plunger 11) the ball is not forced to its seated position by the disc 19. As seen in FIG. 3, with the syringe at an angle to the vertical of more than 45 degrees and with the handle in its innermost position, the ball is not seated on the valve seat.

The preferred range of diameters of ball 31 is from 0.060 inch to 0.180 inch, and of seat 32 is from 0.040 inch to 0.179 inch, it being understood that the diameter of passage 24 is correlated to the ball diameter in such manner that the ball will seat effectively—the diameter of the ball always being greater than that of the seat 32. (As a specific example, the ball 31 is steel and has a diameter of 0.109 inch. Seat 32 and passage wall 26 have a diameter of 0.105 inch.)

It is emphasized that the ball and seat 32 provide an effective check-valve action, being closed during the time when blood is entering the sample chamber 14 by being aspirated into such chamber. Although the ball does not contact the blood because of the interposed filter 12, which is impervious to blood flow, the ball could operate substantially as described if it were placed on the other or inner side of the filter. The specific gravity of the ball is made greater than that of blood, so that the ball will be gravity operated whether or not it is immersed in blood.

The ball 31 is sufficiently heavy that gravity and the conical guide surface 33 will effectively guide it onto its seat 32 despite any frictional or electrostatic forces that may be present. Furthermore, the relationships are caused to be such that the ball will not be guided onto its seat unless the axis of the syringe is at a sufficiently-great angle relative to the horizontal. It is correct and proper that blood samples be taken when the syringe axis is at an angle of not more than about 45 degrees to the vertical (it being assumed, for purposes of illustration and description, that the surface of the skin of the patient at the region surrounding the artery is horizontal). Thus, guide means are provided outwardly adjacent to the valve seat 32 to guide the ball onto the seat when the syringe angle, relative the vertical, is not too large. Preferably, such guide means comprise a frustoconical surface 33 extending from valve seat 32 to the inner end of chamber wall 23. Thus, the frustoconical surface 33 diverges toward the outer end of the syringe. The cone angle of surface 33, relative to the axis of the syringe, is about 45 degrees or somewhat less. In the illustrated embodiment, the cone angle is 35 degrees, because such cone angle causes effective seating of ball 31 on seat 32 when the syringe is at an angle of about 45 degrees to the horizontal. However, if the angle of the syringe were substantiallly less than 45 degrees relative to the horizontal, for example 30 degrees relative thereto, the ball would roll off of its seat 32 so that outward pulling of the plunger 11 by handle 16 for aspiration purposes would be ineffective in that air would vent inwardly from the atmosphere through the described flow-passage means in and around the plunger 11 to the sample chamber 14.

As described in the cited U.S. Pat. No. 4,448,206, the sample chamber contains, preferably, flake heparin. Liquid heparin may also be employed if desired.

DESCRIPTION OF THE METHOD

The nurse or other operator pushes on the handle 16 to move the plunger 11 axially along the syringe body 10 to the extreme inner end of the body, the plunger being stopped by the convergent inner end of such body. This operation of the handle, in the present embodiment, moves the ball 31 close to the seat 32 (see FIG. 3) but does not force the ball to its seat. The operator then makes an arterial puncture so that the hollow needle 34 (FIG. 1) of the syringe penetrates an artery. During such arterial puncture, and subsequently, the syringe is held at an angle, relative to the horizontal, that is greater than 45 degrees.

Assuming that the blood pressure of the individual is sufficiently great, arterial pressure pumps blood through needle 34 into sample chamber 14. The filter will absorb a small portion of blood after thirty seconds and seal itself if the operator does not manually seal the syringe filter. Sample chamber 14 is thus filled, and the air between the blood and the filter 12 is progressively expelled through filter 12 and passage 24, it being understood that, because of the characteristics of the ball as described above, the ball 31 lifts off of its seat 32 and permits the venting of air through the described flow passages. When all air is vented from the sample chamber 14, the blood engages the inner end of filter 12. Such engagement, and the engagement of the blood with the inner end of the plunger body, causes lifting of the plunger 11 as far as desired. Of course, the tubular body 10 is calibrated and is transparent or translucent so that the level of the plunger may be observed and the operation terminated as soon as the plunger has moved outwardly sufficiently far to enlarge the chamber 14 to desired size. A substantially air-free sample has flowed into the sample chamber.

After the needle 34 is withdrawn from the puncture site, the needle end is inserted into a stopper, following which the operator pushes lightly on handle 16. The resulting increased pressure in chamber 14 seals the sample by causing some blood to enter the inner portion of filter 12. Thereafter, the syringe is rotated in order to mix the heparin with the blood.

The above-indicated portion of the method may also be performed by initially setting the plunger 11 at the desired position in the tubular body 10, and then allowing blood to fill the chamber under arterial pressure until the plunger starts to rise. At that time, the needle is withdrawn and the above-indicated stopping and sealing steps are performed.

When there is insufficient arterial pressure to pump blood into chamber 14, the blood is withdrawn by aspiration. Assuming that the plunger 11 is initially at the extreme inner (forward) end of tubular body 10, that is to say at the bottom of the barrel of the syringe, the nurse or other operator may note that the plunger is not rising and thus realizes that there is insufficient arterial pressure. Then, while the syringe is held at an angle of at least 45 degrees relative to the horizontal, the operator pulls gradually on handle 16 to shift plunger 11 upwardly and outwardly, thereby decreasing pressure within chamber 14. Because the angle of the syringe is at least 45 degrees relative to the horizontal, the ball 31 is effectively seated on seat 32, and remains seated, so no air can flow from the ambient atmosphere through the syringe and into sample chamber 14. It follows that the outward movement of the plunger 11 will aspirate blood from the artery into chamber 14, and such aspiration is continued until sufficient blood is drawn.

Thereafter, the syringe is held vertically, with the needle 34 pointing downwardly, after the needle is inserted into a stopper. Then, the handle 16 is again pressed lightly in order to vent air from chamber 14 through the filter and seal the syringe. Then, the syringe is again rotated to mix the heparin as before.

It is emphasized that aspiration may not be effected when the axis of the syringe is less than 45 degrees from the horizontal. This is because the ball 31 is then shifted away (by gravity) from seat 32 as illustrated, for example, in FIG. 4, so that outward shifting of the handle and the plunger do not create large suction in chamber 14, there instead being air passed from the ambient atmosphere through the tubular body 10 and the plunger 11 to the chamber 14. On the other hand, when the syringe is properly oriented, as illustrated (for example) in FIG. 5, the ball 31 is firmly seated on seat 32, so that no air can flow in through the syringe body to the chamber 14, and aspiration is effectively achieved.

There has thus been described a syringe which is position sensitive relative to the aspirating operation, and which will change automatically from the arterial-pressure mode to an aspirating mode without need for any manual valve closing. Instead, there is a gravity valve that effectively seats at all times when the syringe is held at the desired angle to the horizontal. On the other hand, the valve does not seat when the syringe is held at an undesired angle, which prevents aspirating operation at an undesired angle as by an inexperienced operator.

The foregoing detailed description is to be clearly understood as given by way of illustration and example only, the spirit and scope of this invention being limited solely by the appended claims.

What is claimed is:

1. A syringe assembly for taking a blood sample, said assembly comprising:

a tubular body open at a first end thereof and being adapted to receive a hypodermic needle at a second end thereof, a plunger slidably mounted within said tubular body and having a longitudinal passage therethrough, said passage having an air-permeable and blood-impermeable filter therein, a handle connected to said plunger to retract said plunger toward said first end of said tubular body for aspiration of blood, and unidirectional valve means in said plunger, said valve means including ball and seat means in said passage for blocking flow of air through said passage in a direction from said first end to said second end of said tubular body upon retraction of said plunger to create a decreased pressure at said second end of said tubular body, and for permitting a flow of air from said second end to said first end of said tubular body in response to pressure at said second end higher than pressure at said first end, said ball and seat means including gravity-actuated ball means, and further including conical seat means for moving said ball means to said seat means thereby enabling said valve means to block air flow only when the axis of said tubular body is at an angle to the vertical less than a predetermined acute angle with said first end of said tubular body above said second end thereof, said conical seat means moving said ball means from said seat means and preventing blocking of air flow through said passage when the axis of said syringe is at an angle to the vertical greater than said predetermined angle.

2. The invention as claimed in claim 1, in which said valve means comprises a valve chamber within said plunger in communication with said longitudinal passage, said chamber being between said passage and said first end of said tubular body, further comprises a valve seat formed at the end of said passage adjacent said chamber, said chamber having a diameter greater than the diameter of said passage, further comprises a guide surface diverging from said valve seat into said valve chamber, said valve seat and said guide surface being said conical seat means, and further comprises a valve ball confined within said valve chamber and adapted to seat upon said valve seat, said valve ball being said ball means.

3. The invention as claimed in claim 2, in which said ball has a specific gravity greater than the specific gravity of blood and is sufficiently heavy to be gravity driven to seat on said valve seat when the axis of said syringe is at an angle to the vertical less than said predetermined angle, said ball being sufficiently light to be driven from said valve seat to permit flow of air through said passage caused by flow of arterial blood into said syringe.

4. A syringe comprising:

a tubular body open at one end thereof and adapted to receive a hypodermic needle at the other end thereof, a plunger having a longitudinal passageway therethrough, said plunger being slidably mounted in said tubular body, an air-permeable and blood-impermeable filter extending across said passageway adjacent one end of said plunger, said one end of said plunger being relatively adjacent said other end of said tubular body, handle means for retracting said plunger for taking a blood sample by aspiration, a valve chamber formed in the passageway at the other end of said plunger, a valve seat formed in an end of said chamber remote from said other end of said plunger, said valve seat having a diverging guide surface that diverges toward said other end of said plunger, and a ball, of high specific gravity, loosely confined within said valve chamber, said ball being seated and held by gravity upon said valve seat and blocking flow of air through said plunger from said valve chamber to said filter when the syringe is held at a small angle to the vertical and said plunger is retracted to take a blood sample by aspiration, said ball having a weight less than the force exerted thereon by flow of air through said filter to said valve chamber when said syringe is used for taking a sample of blood of normal arterial pressure, whereby said ball is displaced from said valve seat when said syringe is used for taking a sample of blood of normal arterial pressure.

5. The invention as claimed in claim 4, in which said diverging guide surface is a frustoconical guide surface diverging outwardly from said valve seat into said chamber at an angle of not more than about 45 degrees from the axis of said tubular body, whereby said ball may be gravity driven to said seat when the axis of said syringe is at an angle to the vertical that is less than a predetermined angle therefrom, and whereby said ball is prevented by said guide surface from being gravity driven to said seat when the axis of said tubular body is at an angle to the vertical grater than said predetermined angle.

6. The invention as claimed in claim 4, in which said ball is made of steel and has a diameter in the range of about 0.060 inch to about 0.180 inch, and in which the diameter of said seat is in the range of about 0.040 inch to about 0.179 inch and is less than the diameter of said ball.

7. The invention as claimed in claim 4, in which said handle means is slidably mounted in said tubular body, and in which means are provided on said handle means for limiting motion of said ball away from said valve seat.

8. The invention as claimed in claim 4, in which said handle means has an end thereof positioned in said valve chamber, said handle means end being movable relative to said plunger and valve chamber, said handle means end being relatively near said seat and serving to hold said ball near said seat.

9. A syringe assembly for taking a blood sample, said assembly comprising:

a tubular body having first and second ends, said body being open at said first end and being adapted to receive a hypodermic needle at said second end, a plunger slidably mounted in said tubular body, said plunger having a passage provided therein for flow of air longitudinally of said tubular body, said plunger also having a valve chamber therein, said chamber communicating at one side thereof with said passage and at the other side thereof with the ambient atmosphere, said chamber being disposed between said passage and said first end of said tubular body, an air-permeable and blood-impermeable filter mounted in said plunger, said filter being in series relationship to said passage and said chamber so that air from said second end of said tubular body will flow through all three of said filter, said passage and said chamber, a handle connected to said plunger to move said plunger within said tubular body, and a check valve for blocking flow of air in a direction from said first end of said tubular body to said second end of said tubular body, and for permitting flow of air in the opposite direction, said check valve comprising:

a valve seat at said on side of said valve chamber, and a ball disposed loosely within said valve chamber, said valve seat and said ball being so related that said ball will seat on said valve seat when said second end of said tubular body is at an elevation lower than that of said first end of said tubular body and said tubular body is at a substantial angle to the horizontal, said ball having a weight sufficiently great that it will be impelled by force of gravity to seat on said valve seat, despite electrostatic and frictional forces, to close said passage and thus enable negative pressure to be created by retraction of said plunger toward said first end of said tubular body, said ball being sufficiently light to be displaced from said valve seat by pressure of air supplied to said passage due to normal arterial blood pressure, to thus allow venting of air through said plunger during the taking of an arterial blood sample.

10. The invention as claimed in claim 9, in which said ball is made of steel and has a diameter in the range from about 0.06 inch to about 0.180 inch.

11. The invention as claimed in claim 9, in which said ball has a specific gravity substantially greater than that of blood.

12. The invention as claimed in claim 9, in which said valve chamber includes a ball-guiding surface diverging toward said first end of said tubular body, from said valve seat into said valve chamber, said valve chamber having a diameter significantly greater than the diameter of said passage in said plunger, said guide surface cooperating with said ball to enable said ball to be gravity driven onto said valve seat when the axis of said tubular body is at an angle to the vertical that is not greater than a predetermined acute angle and said first end of said tubular body is at an elevation higher than that of said second end thereof, whereby said guide surface will prevent said ball from being gravity driven onto said seat when the axis of said tubular body is at an angle to the vertical greater than said predetermined angle.

13. The invention as claimed in claim 9, in which said air-permeable and blood impermeable filter is interposed between said check valve and said second end of said tubular body.

14. The invention as claimed in claim 9, including means on said handle and plunger for maintaining an air passage between said plunger and said first end of said tubular body.

15. The invention as claimed in claim 9, in which said handle is movably connected to said plunger, and in which means are provided for limiting motion of said handle relative to said plunger between an inner handle position at which said handle is spaced from said valve seat a first distance sufficient to permit said ball to be displaced from said seat, and an outer handle position at which said handle is spaced from said seat a second distance greater than said first distance, whereby said ball is free to move off said valve seat in any position of the handle relative to the plunger.

* * * * *